United States Patent
Mangiardi

(10) Patent No.: US 10,881,498 B2
(45) Date of Patent: Jan. 5, 2021

(54) DEVICE AND METHOD FOR MANAGEMENT OF ANEURISM, PERFORATION AND OTHER VASCULAR ABNORMALITIES

(71) Applicant: Q3 MEDICAL DEVICES LIMITED, Dublin (IE)

(72) Inventor: Eric K. Mangiardi, Charlotte, NC (US)

(73) Assignee: Q3 MEDICAL DEVICES LIMITED, Dublin (IE)

( * ) Notice: Subject to any disclaimer, the term of this patent is extended or adjusted under 35 U.S.C. 154(b) by 105 days.

(21) Appl. No.: 16/375,358

(22) Filed: Apr. 4, 2019

(65) Prior Publication Data

US 2019/0262123 A1    Aug. 29, 2019

Related U.S. Application Data

(63) Continuation of application No. 13/149,327, filed on May 31, 2011, now Pat. No. 10,292,808.

(Continued)

(51) Int. Cl.
| | |
|---|---|
| *A61F 2/07* | (2013.01) |
| *A61F 2/915* | (2013.01) |
| *B05D 1/16* | (2006.01) |
| *D01D 5/00* | (2006.01) |
| *A61L 31/10* | (2006.01) |
| *A61L 31/18* | (2006.01) |

(Continued)

(52) U.S. Cl.
CPC .......... *A61F 2/07* (2013.01); *A61B 17/12109* (2013.01); *A61F 2/82* (2013.01); *A61F 2/915* (2013.01); *A61L 31/10* (2013.01); *A61L 31/18* (2013.01); *B05D 1/16* (2013.01); *B05D 1/36* (2013.01); *D01D 5/0084* (2013.01); *A61F 2/90* (2013.01); *A61F 2002/072* (2013.01); *A61F 2002/075* (2013.01); *A61F 2002/91558* (2013.01); *A61F 2210/0004* (2013.01); *A61F 2220/0008* (2013.01); *A61F 2230/0054* (2013.01); *A61F 2250/0031* (2013.01); *A61F 2250/0067* (2013.01); *B05D 1/18* (2013.01)

(58) Field of Classification Search
CPC ...... A61F 2/07; A61F 2/82; A61F 2/90; A61F 2002/072; A61B 17/12109; A61B 17/12113; A61B 17/12118; D01D 5/0084
See application file for complete search history.

(56) References Cited

U.S. PATENT DOCUMENTS

| | | |
|---|---|---|
| 5,951,599 A | 9/1999 | McCrory |
| 7,244,272 B2 | 7/2007 | Dubson et al. |

(Continued)

OTHER PUBLICATIONS

Yuan, X., et al., "Characterization of Poly(L-lactic acid) Fibers Produced by Melt Spinning", Journal of Applied Polymer Science, vol. 81, pp. 251-260 (2001 ).

(Continued)

*Primary Examiner* — Sarah A Simpson
(74) *Attorney, Agent, or Firm* — Ping Wang; Morris, Manning & Martin LLP

(57) ABSTRACT

This application is directed to a device comprising a covering attached to the device. A process of making a device with a specific covering attached is also disclosed. The application further discloses a method for the treatment of perforations, fistulas, ruptures, dehiscence and aneurisms in luminal vessels and organs of a subject.

21 Claims, 16 Drawing Sheets

Related U.S. Application Data

(60) Provisional application No. 61/344,183, filed on Jun. 7, 2010.

(51) Int. Cl.
*A61F 2/82* (2013.01)
*B05D 1/36* (2006.01)
*A61B 17/12* (2006.01)
*B05D 1/18* (2006.01)
*A61F 2/90* (2013.01)

(56) References Cited

U.S. PATENT DOCUMENTS

| | | |
|---|---|---|
| 7,572,288 B2 | 8/2009 | Cox |
| 7,611,530 B2 | 11/2009 | Pomeranz et al. |
| 2002/0055769 A1 | 5/2002 | Wang |
| 2006/0293743 A1* | 12/2006 | Andersen ............... A61F 2/07 623/1.13 |
| 2007/0067015 A1 | 3/2007 | Jones et al. |
| 2007/0213805 A1 | 9/2007 | Schaeffer et al. |
| 2008/0050419 A1 | 2/2008 | Katsarava et al. |
| 2009/0110713 A1 | 4/2009 | Lim et al. |
| 2009/0138070 A1* | 5/2009 | Holzer ............... A61F 2/07 623/1.15 |
| 2009/0222078 A1 | 9/2009 | Greenberg |
| 2010/0076544 A1 | 3/2010 | Hoffmann et al. |
| 2010/0241214 A1 | 9/2010 | Holzer et al. |
| 2010/0268320 A1 | 10/2010 | Clarke |

OTHER PUBLICATIONS

ZEUS Technical Newsletter, "Eiectrospinning—Fibers at the Nanoscale", 2009 (ZEUS Industrial Products, Inc., Orangeburg, SC).

Kuraishi, K., et al., "Development of Nanofiber-Covered Stents Using Electrospinning: In Vitro and Acute Phase In Vivo Experiments", Journal of Biomedical Materials Research Part B: Applied Biomaterials, pp. 230-239 (2008).

File History of U.S. Appl. No. 13/149,327, filed May 31, 2011.

* cited by examiner

DEVICE AND METHOD FOR MANAGEMENT OF ANEURISM, PERFORATION AND OTHER VASCULAR ABNORMALITIES

This application is a Continuation of U.S. application Ser. No. 13/149,327, filed May 31, 2012, which claims the benefit of U.S. Provisional Application Ser. No. 61/344,183, filed Jun. 7, 2010. The entirety of the aforementioned application is incorporated herein by reference.

FIELD

This application generally relates to devices and methods for the treatment of wounds in luminal vessels and organs, and other vascular abnormalities. In particular, the invention relates to a device and methods for the treatment of perforations, fistulas, ruptures, dehiscence, punctures, incisions, and aneurisms in luminal vessels and organs of a subject.

BACKGROUND

Current means of treating perforations in luminal vessels and organs is through operative procedures, endoscopic suturing, vascular closure devices, or with an implant used for perforation management. However, current implants are big and have bulky coverings, are difficult to use, are not widely accepted, and are, in many cases, only used as a means of last resort.

Aneurisms occur when an artery balloons out due to increased blood pressure or a weakening in a blood vessel. Aneurisms can occur throughout the body. Brain aneurisms, also known as intracranial or cerebral aneurisms, are life-threatening, particularly if they rupture. Once an aneurysm forms, it will not disappear on its own. Medication may help slow its growth, but is not a cure. Most aneurisms eventually need repair.

For the treatment of berry or saccular aneurisms, one current therapy is endovascular coiling, wherein a catheter is inserted into the femoral artery in the groin, through the aorta, into the brain arteries, and finally into the aneurysm itself. Once the catheter is in the aneurysm, platinum coils are pushed into the aneurysm sac and released to allow the aneurysm to clot or to change the turbulent flow and stop growing through a release or diversion of pressure. In another current therapy, the aneurysm is surgically treated by performing a craniotomy, exposing the aneurysm, and closing the base of the aneurysm with a clip.

For fusiform aneurisms, a current treatment strategy is to place grafts that do not degrade. These grafts have a history of collecting thrombi that can break off and get pushed further downstream. Another current treatment strategy is the surgical option of performing a bypass which is technically challenging and has many complications on its own.

SUMMARY

One aspect of the present invention relates to a device for aneurism and perforation management. The device comprises a rigid, stent like body and an electrospun fibrous covering that covers the stent like body for increased stability during placement.

In one embodiment, the stent like body comprises a biodegradable or bioabsorbable material.

In another embodiment, the biodegradable or bioabsorbable material comprises magnesium, iron, a polymer or co-polymer material.

In another embodiment, the stent like body comprises a non-biodegradable or non-bioabsorbable material.

In a related embodiment, the non-biodegradable or non-bioabsorbable material comprises stainless steel, cobalt chromium, or other alloy or a non-degradable polymer.

In another embodiment, the fibrous covering comprises a biodegradable or bioabsorbable material.

In a related embodiment, the biodegradable or bioabsorbable material comprises a poly-($\alpha$-hydroxy acid) or poly-(L-lactic acid).

In another embodiment, the fibrous covering comprises a non-biodegradable or non-bioabsorbable material.

In another embodiment, the covering material is mixed with barium sulphate or other illuminating material.

In another embodiment, the stent like body is coated with a layer of biodegradable material and wherein the fibrous covering covers the layer of biodegradable material.

In a related embodiment, the stent like body is coated with the layer of biodegradable material by dip-coating.

In another embodiment, the stent like body is treated or etched with chemical agents, laser or abrasives to allow more effective attachment of the electrospun fibrous covering to the stent like body.

In another embodiment, the stent like body is expandable.

Another aspect of the present invention relates to a method of making device for aneurism and perforation management. The method comprises dipping a rigid, stent like body in a biodegradable coating material to form a coated stent like body; and electrospinning fibers of a covering material onto the coated stent like body.

In one embodiment, the coated stent like body is covered by electrospinning in a way that the fibers cross one another interlocking and forming angles.

Another aspect of the present invention relates to a method for occluding an opening in a luminal vessel. The method comprises placing at the opening a device comprising an expandable stent like body coated with a biodegradable material and an electrospun fibrous covering that covers the stent like body; and expanding the stent like body to immobilize the device at the opening.

In one embodiment, the luminal vessel is an artery or a vein.

In another embodiment, the opening is an aneurysm, perforation, rupture or fistula.

In a related embodiment, the aneurysm is a berry aneurysm or a fusiform aneurysm.

In another related embodiment, the aneurysm is a cerebral, cardiac, pulmonary or aortic aneurysm.

Another aspect of the present invention relates to a method for treating condition in a luminal vessel in a subject. The method comprises introducing into the subject a device comprising an expandable stent like body that is coated with a biodegradable material and covered with an electrospun covering; positioning the device at a treatment site; and expanding the expandable stent like body to immobilize the device at the treatment site.

In one embodiment, the expandable stent like body comprises magnesium, iron or a polymer material.

In another embodiment, the condition is plaque in a blood vessel.

In another embodiment, the condition is an acute myocardial infarction.

In another embodiment, the condition is a hole or an opening in said luminal vessel.

In another embodiment, the condition is a grafted vessel. The device is emplaced under the graft to support the graft during the healing process and prevent leakage at sutures.

In another embodiment, the device covering can be further coated with a drug coating that can be eluted to minimize hyperplastic response or to induce closure of the aneurysm.

DETAILED DESCRIPTION

Figure 1A:
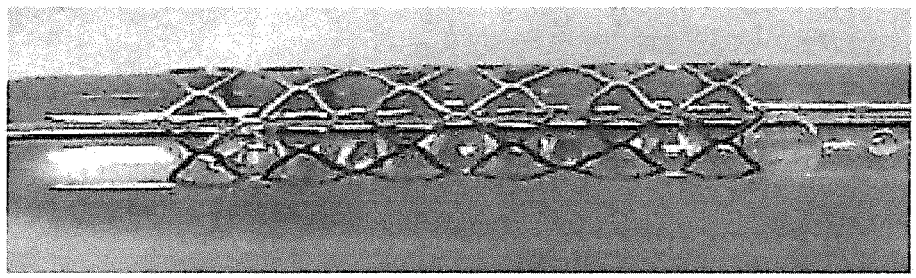
FIGS. 1A-D show exemplary stent devices composed of bioabsorbable materials such as: (A) magnesium, (B) iron, (C) composite material, and (D) a bioabsorbable covering.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention.

One aspect of the present invention relates to a device for aneurism and perforation management. The device comprises a stent like body and a covering that covers the stent like body for increased stability during placement. In other embodiments, the device may further comprise other supporting structure used for the implant. The device can be used to treat abnormal openings, such as perforations, fistulas, dehiscents, and aneurisms, in luminal vessels and organs. The device can be implanted into the neurovascular, peripheral vascular, coronary, cardiac, and renal systems, among others. The device allows the occlusion of a leak or weakening in a vessel wall, whereby the device reestablishes a normal passage long enough for the lumen to heal.

The shape and the size of the stent like body may vary depending on the application of the device. The stent like body can be a stent or an expandable stent. It is well known in the art that a stent is a device used to support a bodily orifice, cavity, vessel, and the like to reinforce collapsing, dissected, partially occluded, weakened, diseased or abnormally dilated or small segments of a vessel wall. The stent like body may be in any suitable form, including, but not limited to, scaffolding, a tube, a slotted tube or a wire form. The stent like body may be rigid, resilient, flexible, and collapsible with memory. In one embodiment, the stent like body comprises a biodegradable or bioabsorbable material.

The material covering the stent like body will biodegrade and the stent like body will remain if it is made from a non-biodegradable, non-bioabsorbable material. In certain embodiments, the stent like body is also made from a biodegradable or bioabsorbable material, and will degrade after the degradation of the biodegradable covering. In other embodiments, the stent like body is made from a biodegradable or bioabsorbable material, and is partially covered with the biodegradable covering so that it will degrade with the biodegradable covering at the same time but at a slower rate.

In one embodiment, the covering is an electrospun fibrous covering comprising a biodegradable material. In another embodiment, the covering is attached to the stent like body by dip-coating process. In another embodiment, the stent like body is first coated with a biodegradable layer by dip-coating process and then covered with an electrospun fibrous biodegradable covering.

In one embodiment, the covering covers the entire stent like body. In another embodiment, the covering covers a portion of the stent like body. In another embodiment, the covering covers a majority of the stent like body but leaves open an end portion of the stent like body. In another embodiment, the covering covers a majority of the stent like body but leaves open a middle section of the stent like body.

The device is designed to occlude the abnormal opening long enough for it to heal or, in the case of an aneurysm, for it to occlude the aneurysm, be it a berry or fusiform aneurysm. Without wishing to be bound by theory, it is believed that the coating and/or the covering allows the device to support the vessel wall or luminal wall over a greater surface area, thereby reducing the risk of a hyperplastic response. The covering may contain, or is further coated with, an agent that reduces hyperplastic response.

As used herein, the term "biodegradable material" or "bioresorbable material" refers to a material that can be broken down by either chemical or physical process, upon interaction with the physiological environment at the implantation site, and erodes or dissolves within a period of time, typically within days, weeks or months. A biodegradable or bioresorbable material serves a temporary function in the body, such as supporting a lumen or drug delivery, and is then degraded or broken into components that are metabolizable or excretable.

In some embodiments, the stent like body of the device is first coated with a biodegradable material through a dip-coating process and then covered with the covering by electrospinning. The coating allows the covering to adhere more effectively to the stent like body of the device. The coating may contain the same material as the biodegradable material of the covering, or another biodegradable material around the stent struts to promote adherence of the electrospun covering.

In particular embodiments, the stent like body is treated or etched with chemical agents, laser and/or abrasives to allow the electrospun covering to adhere more effectively to the stent like body or other supporting structure used for the implant. In such embodiments, the stent like body itself or the other supporting structure used for the implant may or may not be coated with a biodegradable material prior to electrospinning.

The stent like body can be made of a biodegradable or bioabsorbable material including, but not limited to, bioabsorbable metals or alloys and biodegradable polymer materials.

Examples of bioabsorbable metals and alloys include, but are not limited to, lithium, sodium, magnesium, aluminum, potassium, calcium, cerium, scandium, titanium, vanadium, chromium, manganese, iron, cobalt, nickel, copper, zinc, gallium, silicon, yttrium, zirconium, niobium, molybdenum, technetium, ruthenium, rhodium, palladium, silver, indium, tin, lanthanum, praseodymium, neodymium, promethium, samarium, europium, gadolinium, terbium, dysprosium, holmium, erbium, thulium, ytterbium, lutetium, tantalum, tungsten, rhenium, platinum, gold, lead and alloys thereof.

In certain embodiments, the stent like body is made from an alloy comprising a combination of material that will decompose in the body comparatively rapidly, typically within a period of several months, and form harmless constituents. To obtain uniform corrosion, the alloy may comprise a component, such as magnesium, titanium, zirconium, niobium, tantalum, zinc or silicon, which covers itself with a protective oxide coat. A second component, such as lithium sodium, potassium, calcium, iron or manganese, which possesses sufficient solubility in blood or interstitial fluid, is added to the alloy achieve uniform dissolution of the oxide coat. The corrosion rate can be regulated through the ratio of the two components.

Preferably, the alloy is to be composed so that the corrosion products are soluble salts, such as sodium, potassium, calcium, iron or zinc salts, or that non-soluble corrosion products, such as titanium, tantalum or niobium oxide originate as colloidal particles. The corrosion rate is adjusted by way of the composition so that gases, such as hydrogen which evolves during the corrosion of lithium, sodium, potassium, magnesium, calcium or zinc, dissolve physically, not forming any macroscopic gas bubbles.

Alternatively, the stent like body can be made of a non-biodegradable and non-bioabsorbable material including, but not limited to, stainless steel, titanium, chromium cobalt or a non-degradable polymer. The stent like body can also be made of any suitable pharmaceutically acceptable alloy comprising, but not limited to, iron, magnesium, manganese, titanium, carbon, chromium, cobalt, molybdenum, nickel, aluminum, vanadium, zirconium, niobium, and/or tantalum. In some embodiments, the stent like body can also be made from a ceramic.

The covering of the device can be made of a biodegradable or bioabsorbable material such as, but not limited to, a poly-(α-hydroxy acid), preferably poly-(L-lactic acid). In a further embodiment, the covering material can be mixed with barium sulphate or other illuminating material to insure proper placement and visibility during the deployment using fluoroscopy, x-ray, or other imaging modalities.

In a particular embodiment, the biodegradable or bioabsorbable material for the covering of the device is formulated to begin to degrade in no less than 15 days after the device is emplaced in the subject. In another embodiment, the biodegradable or bioabsorbable material for the covering of the device is formulated to begin to degrade in no less than 30 days after the device is emplaced in the subject. In a further embodiment, the biodegradable or bioabsorbable material for the covering of the device is formulated to begin to degrade in no less than 45 days after the device is emplaced in the subject. In still another embodiment, the biodegradable or bioabsorbable material for the covering of the device is formulated to begin to degrade in no less than 60 days after the device is emplaced in the subject. In yet another embodiment, the biodegradable or bioabsorbable material for the covering of the device is formulated to begin to degrade in no less than 90 days after the device is emplaced in the subject.

In a certain embodiment, the biodegradable or bioabsorbable material for the covering of the device is formulated to fully degrade within 90 days after the device is emplaced in the subject. In a further embodiment, the biodegradable or bioabsorbable material for the covering of the device is formulated to fully degrade within 120 days after the device is emplaced in the subject. In another embodiment, the biodegradable or bioabsorbable material for the covering of the device is formulated to fully degrade within 150 days after the device is emplaced in the subject. In still another embodiment, the biodegradable or bioabsorbable material for the covering of the device is formulated to fully degrade within 180 days after the device is emplaced in the subject. In yet another embodiment, the biodegradable or bioabsorbable material for the covering of the device is formulated to fully degrade within one year after the device is emplaced in the subject.

In one embodiment, the covering of the device comprises a copolymer made from 34% lactide, 35% caprolactone, 14% trimethylene carbonate, and 17% glycolide. The copolymer may be deposited on the stent like body by electrospinning or by film coating. The copolymer coating would provide strength retention for 30-60 days and mass absorption in 9-12 months.

Initial coating of the strut segments of the stent like body has the benefit and importance of insuring the coating thickness is much thicker at an area close to the struts, becoming thinner moving away from struts to the center of a cell, allowing degradation to occur in the middle of the covering in the cell structure of the stent as well as allowing for controlled opening and crimping of the device during manufacturing and deployment in the target lesions. This particular embodiment allows the covering of the device to gradually degrade from the center of the cell towards the struts, and allows the device covering to maintain increased applied force to keep the covering in place against the luminal wall during the degradation period.

In one embodiment, the stent like body itself is made from a biodegradable material so that it will be degraded after the degradation of the covering. In another embodiment, the stent like body itself is made from a biodegradable material and is partially covered with the covering so that the stent like body will start degradation at the same time with the covering but at a slower rate. Electrospinning orientation is further enhanced through the adherence to the covered strut giving it greater elasticity and the ability to orient to insure the maximum range of opening and closing of the device without tearing the covering. This technique of applying the coverings allows the manufacture of a device with a very low profile of the covering material to cover the support device and insure ease of delivery. Further, the elastic coverings of the present invention allow an expandable stent like body, whether it is balloon expandable or self expanding, to open to its nominal diameter. This is not possible based on the existing art. In one embodiment, the struts of the stent like body are encased in the covering material in a circular form to provide the adherence.

Examples of biodegradable polymers include, but are not limited to, polydioxanone, polycaprolactone, polygluconate, poly(lactic acid) polyethylene oxide copolymer, modified cellulose, polyhydroxybutyrate, polyamino acids, polyphosphate ester, polyvalerolactone, poly-ε-decalactone, polylactonic acid, polyglycolic acid, polylactides, polyglycolides, copolymers of the polylactides and polyglycolides, poly-ε-caprolactone, polyhydroxybutyric acid, polyhydroxybutyrates, polyhydroxyvalerates, polyhydroxybutyrate-co-valerate, poly(1,4-dioxane-2,3-one), poly(1,3-dioxane-2-one), poly-para-dioxanone, polyanhydrides, polymaleic acid anhydrides, polyhydroxy methacrylates, fibrin, polycyanoacrylate, polycaprolactone dimethylacrylates, poly-1-maleic acid, polycaprolactone butyl acrylates, multiblock polymers from oligocaprolactonediols and oligodioxanonediols, polyether ester multiblock polymers from PEG and poly (butylene terephthalates), polypivotolactones, polyglycolic acid trimethyl carbonates, polycaprolactone glycolides, poly (γ-ethyl glutamate), poly(DTH-iminocarbonate), poly(DTE-co-DT-carbonate), poly(bisphenol A-iminocarbonate), poly-orthoesters, polyglycolic acid trimethyl carbonate, polytrimethyl carbonates, polyiminocarbonates, poly(N-vinyl)-pyrrolidone, polyvinyl alcohols, polyester amides, glycolized polyesters, polyphosphoesters, polyphosphazenes, poly[p-carboxyphenoxy)propane], polyhydroxy pentanoic acid, polyanhydrides, polyethylene oxide propylene oxide, soft polyurethanes, polyurethanes having amino acid residues in the backbone, polyetheresters such as polyethylene oxide, polyalkene oxalates, polyorthoesters as well as copolymers thereof, lipids, carrageenans, fibrinogen, starch, collagen, protein based polymers, polyamino acids, synthetic polyamino acids, zein, polyhydroxyalkanoates, pectic acid, actinic acid, carboxymethyl sulfate, albumin, hyaluronic acid, chitosan and derivatives thereof, heparan sulfates and derivates thereof, heparins, chondroitin sulfate, dextran, O-cyclodextrins, copolymers with PEG and polypropylene glycol, gum arabic, guar, gelatin, collagen N-hydroxysuccinimide, lipids, phospholipids, polyacrylic acid, polyacrylates, polymethyl methacrylate, polybutyl methacrylate, polyacrylamide, polyacrylonitriles, polyamides, polyetheramides, polyethylene amine, polyimides, polycarbonates, polycarbourethanes, polyvinyl ketones, polyvinyl halogenides, polyvinylidene halogenides, polyvinyl ethers, polyisobutylenes, polyvinyl aromatics, polyvinyl esters, polyvinyl pyrrolidones, polyoxymethylenes, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, EPDM gums, fluorosilicones, carboxymethyl chitosans polyaryletheretherketones, polyetheretherketones, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulfones, epoxy resins, ABS resins, EPDM gums, silicones such as polysiloxanes, polydimethylsiloxanes, polyvinyl halogens and copolymers, cellulose ethers, cellulose triacetates, chitosans and copolymers and/or mixtures of the aforementioned polymers.

In a particular embodiment, the device comprises visibility or opacity technology allowing visualization of the device using an imaging means or imbedding the covering or strut coating with the same or various drugs or illuminating material. In another embodiment, the covering allows the stent to freely float or to move in a controlled manner under the coating and covering, with the level of restriction depending on the thickness of said covering or coating. In another embodiment, the covering or coating has varying degrees of degradation. If the covering was formed by the electrospinning, the filaments would be intertwined and set with such angles to allow the stent to be crimped and opened as required in normal applications and the degradation could be controlled by the density of the material established by the number of filament crossings and the angles to absorb the load and stresses of opening and closing and anatomical compressions. Furthermore, the material of the support, coating and covering of the device allow normal body fluids to flow unobstructed. In yet another embodiment, the device is covered in a single layer, double layer, triple layer or multiple layers depending on the need. The covering can be on the outside of the stent like body, on the inside of the stent like body, or encapsulating the of the stent like body.

In another embodiment, the device comprises a therapeutically effective amount of a therapeutic agent or agents. In particular embodiments, the device comprises at least one therapeutic agent. In other embodiments, the device comprises one therapeutic agent or more than one therapeutic agent. In still other embodiments, the device comprises two, at least two, three, four, or five therapeutic agents. In a particular embodiment, a therapeutic agent comprised on the device is an analgesic or anesthetic agent. In another particular embodiment, a therapeutic agent comprised on the device is an antibiotic, antimicrobial, antiviral, or antibacterial agent. In another embodiment, a therapeutic agent comprised on the device is a thrombotic or coagulant agent. In another embodiment, a therapeutic agent comprised on the device is an anti-thrombotic or anticoagulant agent.

In certain embodiments, the therapeutic agent is comprised in a pharmaceutical composition formulated for sustained-release. Sustained-release, also known as sustained-action, extended-release, time-release or timed-release, controlled-release, modified release, or continuous-release, employs a pharmaceutically acceptable agent that dissolves slowly and releases the therapeutic agent over time. A sustained-release formulation allows the topical release of steady levels of the therapeutic agent directly at the site where it would be therapeutically effective.

In one embodiment, the pharmaceutical composition is formulated for sustained release by embedding the active ingredient in a matrix of insoluble substance(s) such as acrylics or chitin. A sustained release form is designed to release the therapeutic agent at a predetermined rate by maintaining a constant drug level for a specific period of time. This can be achieved through a variety of formulations, including, but not limited to liposomes and drug-polymer conjugates, such as hydrogels.

In another embodiment, the therapeutic agent is comprised in a pharmaceutical composition formulated for delayed-release, such that the therapeutic agent is not immediately released upon administration. An advantage of a delayed-release formulation is that the therapeutic agent is not released from the device until the device has been emplaced in the desired location. In some embodiments, the therapeutic agent is first coated onto the device and is then coated over with a pharmaceutical composition formulated for delayed-release.

In a particular embodiment, the therapeutic agent is delivered in a vehicle that is both delayed release and sustained release.

In another embodiment, a therapeutic agent comprised on the device is applied to the exterior surface of the device. A therapeutic agent may be applied to the exterior of the cover or may be mixed or imbedded into the covering material. In some embodiments, the device may contain an additional coating on its exterior that delays the release of the therapeutic agent or modulates the release of the therapeutic agent over time. In one embodiment, the covering of the device is further coated with a drug coating that can be eluted to minimize hyperplastic response or to induce closure of the aneurysm.

Figure 1B:
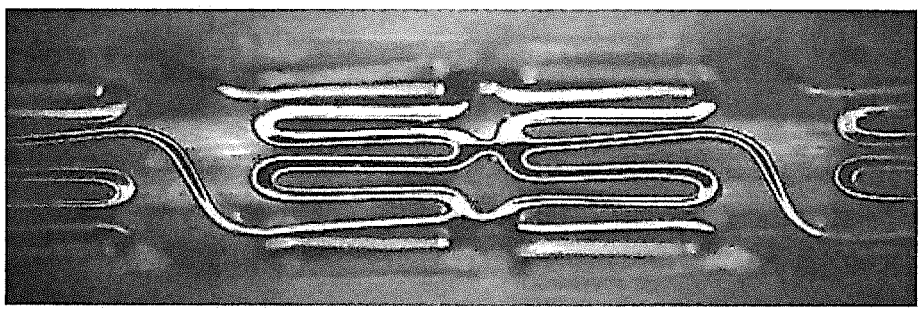
Figure 1C:
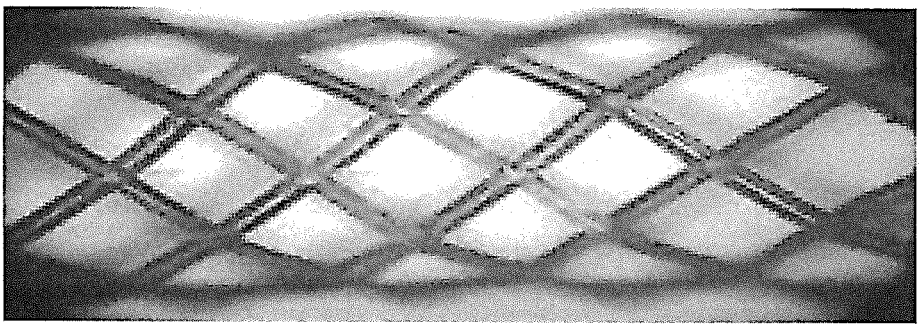
Figure 1D:
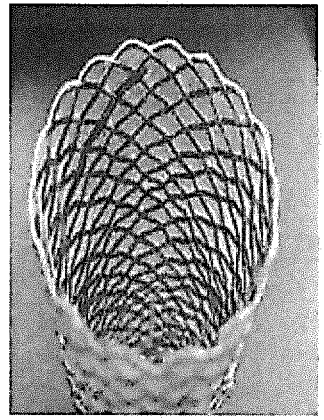

In another embodiment, a therapeutic agent comprised on the device is applied to the interior surface of the device. In further embodiments, therapeutic agents are applied to both the interior and to the exterior surfaces of the device. Therapeutic agents applied to the interior and exterior surfaces of the device may be the same or different. As a non-limiting example, a coagulant agent may be applied to the exterior surface of the device to facilitate the healing of a perforation, while an anti-coagulant may be applied to the interior of the device to prevent restriction of the flow of bodily fluids and cells through the device Various biodegradable or bioabsorbable implants can be used in the coronary, peripheral vascular, or non-vascular space that could be covered with the electro spinning process or dip-coated process to be used to occlude various defects or leaks. Exemplary materials include, but are not limited to, magnesium (FIG. 1A), iron (FIG. 1B), or polymer materials (FIG. 1C). Coverings of the device (FIG. 1D) can also be made of biodegradable or bioabsorbable materials.

Figure 2:
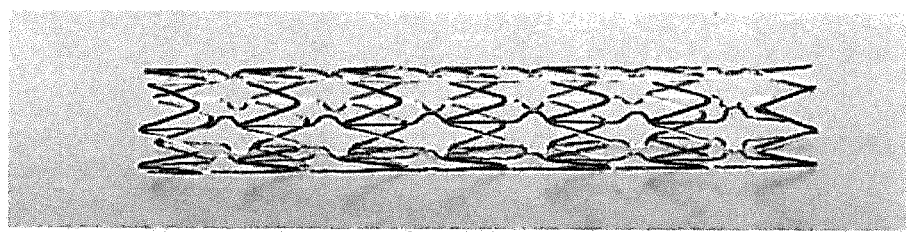
FIG. 2 shows an exemplary stent device composed of a non-biodegradable material.

The device can also be made from a material that is not biodegradable and that is a more traditional and commonly used material such as, but not limited to, stainless steel, titanium or cobalt chromium (FIG. 2). The device can also be made of any suitable pharmaceutically acceptable alloy comprising, but not limited to, iron, titanium, carbon, chromium, cobalt, molybdenum, nickel, aluminum, vanadium, zirconium, niobium, and/or tantalum. The stent like body of the device can also be made from a ceramic. This stent like body would be coated or spun in the tube diameter it was cut from, or some other diameter from about 50% less the tube diameter to about 100% of its maximum expanded diameter which is an embodiment of this process to assist with the expansion of the stent.

Figure 3:
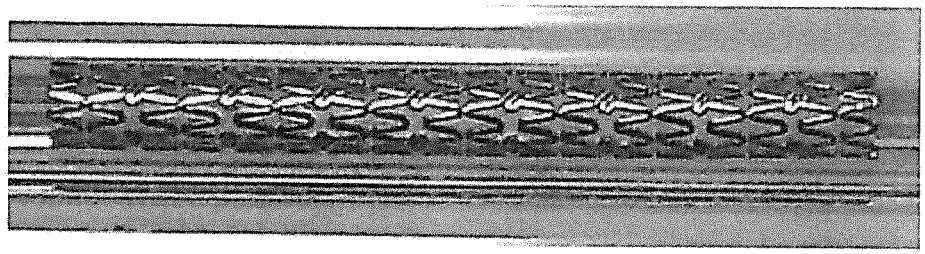
FIG. 3 shows an exemplary stent device crimped onto a catheter after dip-coating or electrospinning.

The device can be crimped to its nominal diameter on a catheter (FIG. 3) after it is covered from an electrospinning or dip-coated process.

Use of the Device

A further aspect of the present invention is a method of treating an aneurysm or occluding an opening in a luminal vessel in a mammal using the device of the present invention.

In another embodiment, the opening in the luminal vessel has been sutured, stapled, cauterized or glued and the device is used to support the luminal wall during the healing process and prevent leakage.

The aneurysm may be a cerebral aneurysm, an aortic aneurysm or a peripheral aneurysm. The form of the aneurysm may be fusiform, saccular or berry.

The device may also be used in the treatment of a perforation, fistula, or dehiscent in a vessel.

A further embodiment for use of the present invention is carotid stenting, wherein placement of the device prevents a plaque from breaking off during stent placement and to insure the plaque is trapped behind the implant until the covering dissolves.

Another embodiment is in the treatment of an acute myocardial infarction, wherein placement of the device traps a thrombus or other such material or plaque against the luminal wall to prevent the thrombus from being pushed down stream.

A further embodiment for use of the present invention is in association with graft placement, wherein the device is emplaced under a graft to support it during the healing process and prevent leakage at the sutures.

In each of these methods, the method comprises the steps of (a) introducing into the subject a device comprising (i) a stent like body coated with a biodegradable material, and (ii) an electrospun fibrous biodegradable covering that covers said stent like body, (b) positioning the device adjacent to the area in need of treatment, and (c) expanding the device to allow it stays at the treatment site.

After implantation, the material covering the stent like body will biodegrade and the stent like body will remain if it is made from a non-biodegradable, non-bioabsorbable material. In certain embodiments, the stent like body is also made from a biodegradable or bioabsorbable material, and will degrade after the degradation of the biodegradable covering. In other embodiments, the stent like body is made from a biodegradable or bioabsorbable material, and is partially covered with the biodegradable covering so that it will degrade with the biodegradable covering at the same time but at a slower rate.

Dip-Coating

Figure 4:
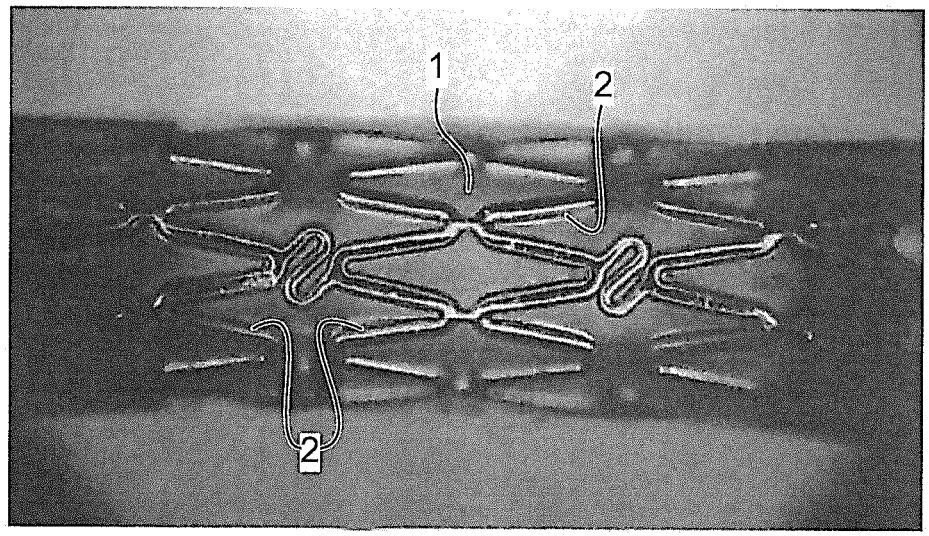
FIG. 4 shows an exemplary stent device in dipped form.
Figure 5:
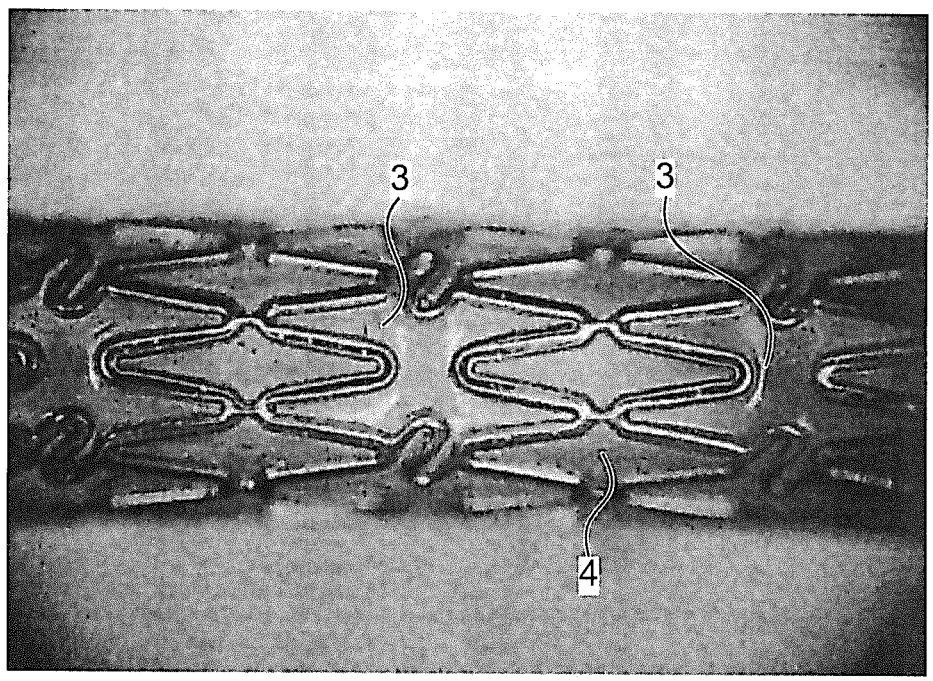
FIG. 5 shows a magnified view of the stent device of FIG. 4.

Stent in dip-coated form (FIG. 4) has an increased covering thickness around the strut segments to allow for expansion, having ripples 1 in the material that will allow it to expand beyond the current state. The device with a higher thickness or density of coating starting with the individual struts and then dip-coated again after to insure that the device covering will degrade from the middle of the cell 2 to the struts. Higher magnification (FIG. 5) shows that the covering is thicker around the arch of the stent 3 and tapers off as you move away from the struts. The covering is much thinner in the middle of the cell 4 than close to the struts, allowing the device to biodegrade from the middle of the cell to the strut segments versus at the attachment points to the struts.

Electrospinning

The process of electrospinning can be carried out by any method known in the art. The method used in the present invention is not to be limited to a single method of electrospinning. Exemplary, non-limiting, processes for electrospinning are described, for example, by Yuan, X et al. (Yuan, X et al. Characterization of Poly-(L-Lactic Acid) Fibers Produced by Melt Spinning. J. Appl. Polym, Sci. 2001, 81:251-260.) and in ZEUS Technical Newsletter, Electrospinning—Fibers at the Nano-scale. 2009 (Zeus Industrial Products, Inc., Orangeburg, S.C.).

In the coating of the device by electrospinning, the device is covered in a way that the fibers cross one another interlocking and forming angles. In one embodiment, the fibers intersect one another at angles with angles from about 1, 5, 10, 15, 20, 25, 30, 35, 40 or 45 degrees to about 45, 50, 55, 60, 65, 70, 75, 80, 85, 90 or 95 degrees. In another embodiment, the fibers intersect one another at angles with angles from about 1 degree to about 95 degrees. In a further embodiment, the fibers intersect one another at angles with angles from about 5 degrees to about 95 degrees. In another embodiment, the fibers intersect one another at angles with angles from about 10 degrees to about 90 degrees.

The fibers are overlapped to allow for the stresses during crimping, loading, and expansion to be born by all the materials filaments with the stress loads being on the various filaments and their respective angles which allows the distribution of the stresses and the loads in all directions versus a uniform direction which is required for the opening and closing of a cylindrical tube of varying lengths. In one embodiment, the fibers are overlapped a minimum of about 1 time and a maximum of about 1000 times. In a preferred embodiment, the fibers are overlapped a minimum of about 1 time and a maximum of about 500 times. In another preferred embodiment, the fibers are overlapped a minimum of about 2 times and a maximum of about 500 times. Yet in another preferred embodiment, the fibers are overlapped a minimum of about 2 times and a maximum of about 400 times. In still another preferred embodiment, the fibers are overlapped a minimum of about 2 times and a maximum of about 300 times. In a more preferred embodiment, the fibers are overlapped a minimum of about 2 times and a maximum of about 200 times. In a most preferred embodiment, the fibers are overlapped a minimum of 2 times and a maximum of 200 times.

Figure 6:
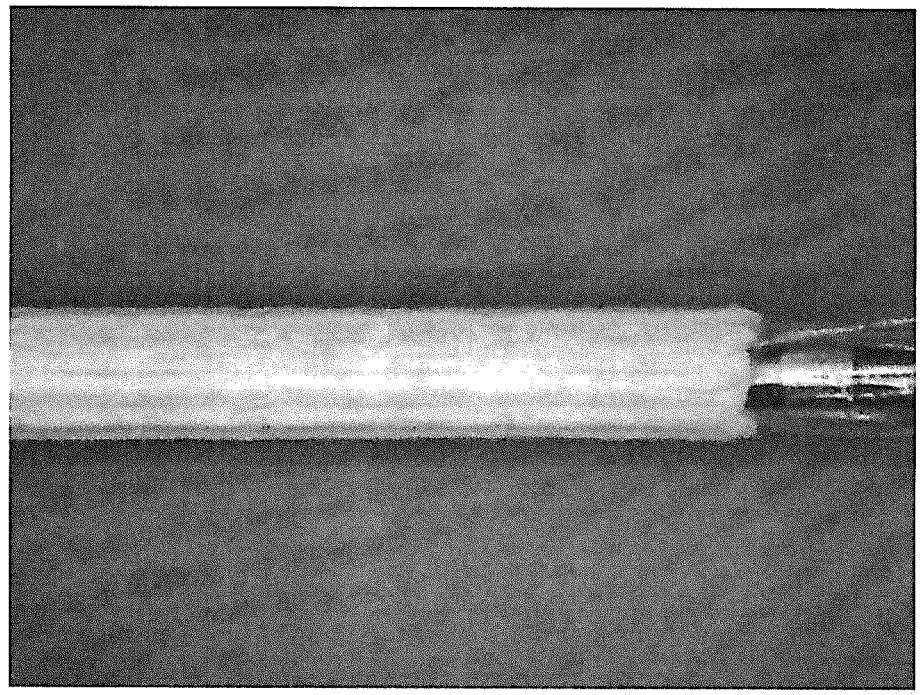
FIG. 6 shows a crimped stent device comprising a covering of fibers applied with electrospinning.
Figure 7:
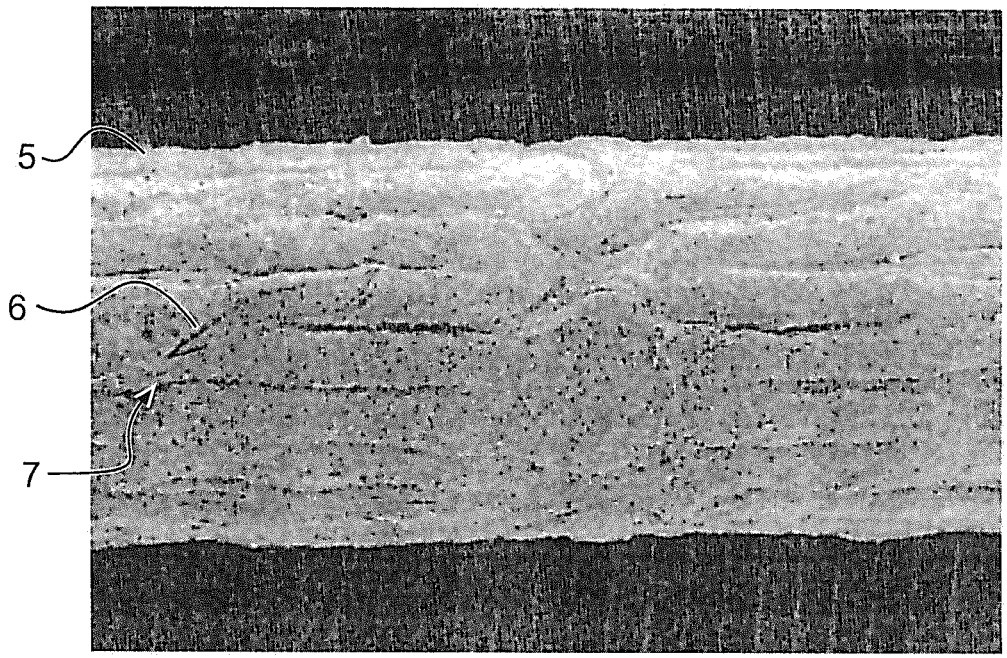
FIG. 7 shows a stent device comprising a covering of fibers applied with electrospinning in a crimped state.

FIG. 6 shows a crimped stent that has an electrospun covering. A magnified view of the same stent (FIG. 7) in its crimped state shows the electrospun fibers with mesh like cross section fibers 5. An angle 6 of the electrospun material allows the device to be opened to its full expansion through the use of the preformed angle of the electrospun material. Shapes which form in the mesh, such as a triangle 7, circles, rectangles, or ovals allow the device to expand to its optimal diameter. This design shows that through the use of various geometrical shapes the device can expand without putting fibers under strains that cause them to break.

Figure 8:
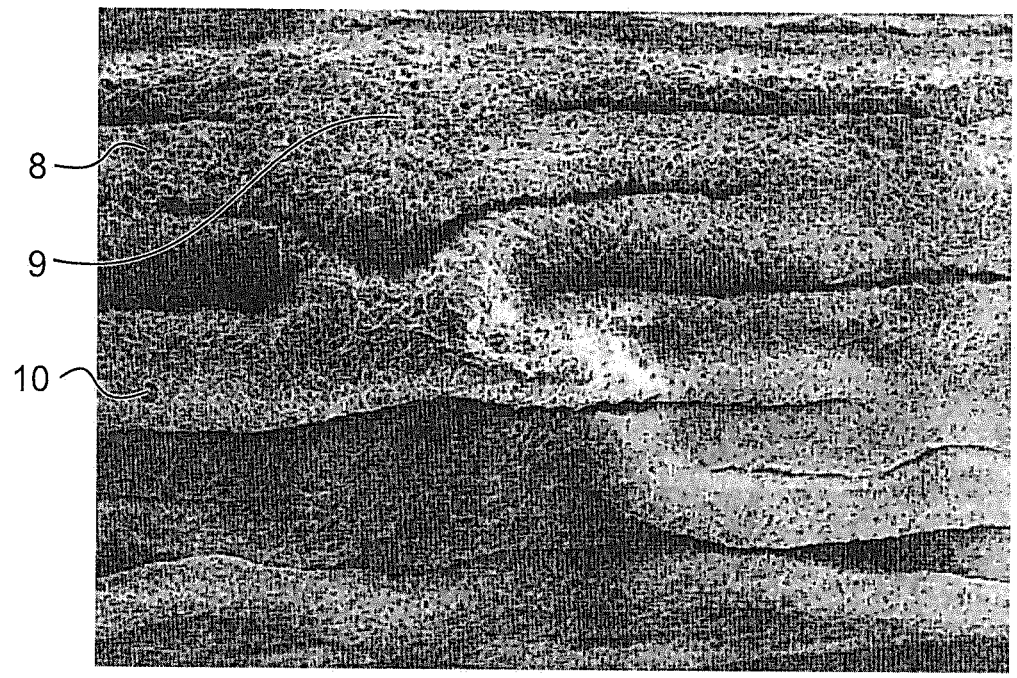
FIG. 8 shows a magnified view of the stent device of FIG. 7.

An electrospun stent may have a porous structure (FIG. 8) in a honeycomb pattern or circle chain links that allow the covering to expand during the opening process of the device. This porous structure can comprise large interlocking circles 8, a deep honeycomb structure 9, and small circular structures 10 that allow for expansion and ease of drug loading as well as visibility material.

Figure 9:
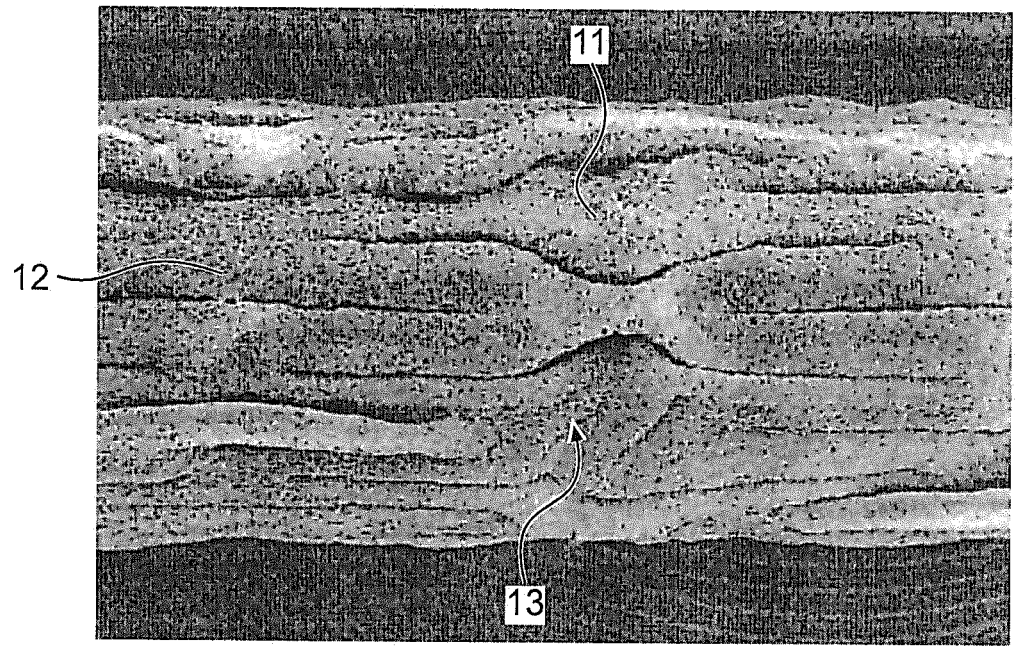
FIG. 9 shows the small circular structure within a covering of fibers applied with electrospinning.

In a device having a covering formed by an electrospinning apparatus having a conical circular opening that release the polymers (FIG. 9), variation in the strand fibers and the hole sizes 11 are regulated and oriented by changes in heat, viscosity of the material and molecular chain lengths. Modifying the opening of the dispersion tube that releases the material to be electrospun can modify the covering fiber thickness.

One can further modify the flow and alignment of the polymer fibers by changing the opening shape from a circle to one in the shape of an oval, cross, diamond, star, octagon, other polygons or other such shapes. Additionally, the dispersing tube can have a tapered inner surface of varying shapes that can also modify the process of alignment or application. Additionally, because the material and the receiving device have different charges, you can further control the fiber application by reversing the direction of the application device versus moving the coated device to modify the fiber orientation. By moving the applicator cone versus the device in the opposite or in the direction of the desired laying down of the fibers one can better control the fiber angles, shapes, and thickness to achieve the desired or optimal results. The shape of the holes 12, 13 can also be varied by the application procedure.

Figure 10:
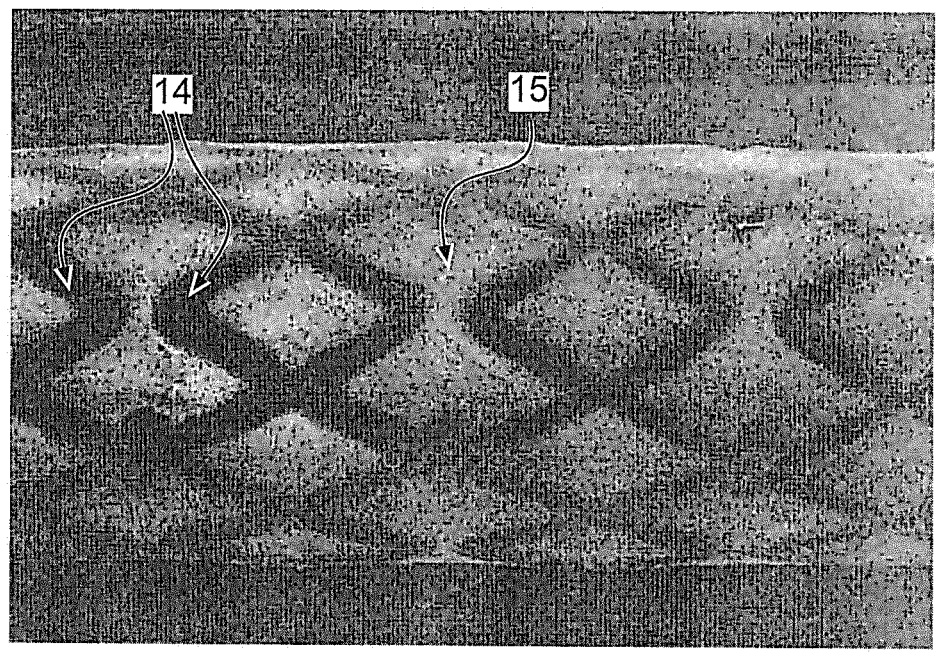
FIG. 10 shows electrospun fiber attached to stent device struts that have been previously covered with electrospun material.

Electrospun fiber can be attached to struts that have been previously covered with electrospun material (FIG. 10) to insure that the struts have a thicker amount of material than the center of the cell and that the material has increase sticking and elastic characteristics. In this case, the denser more fibrous adherence is aligned on the struts 14, while the center of the cells 15 have less of the covering but still have the porous and cross sectional aspect of the fibers.

Figure 11:
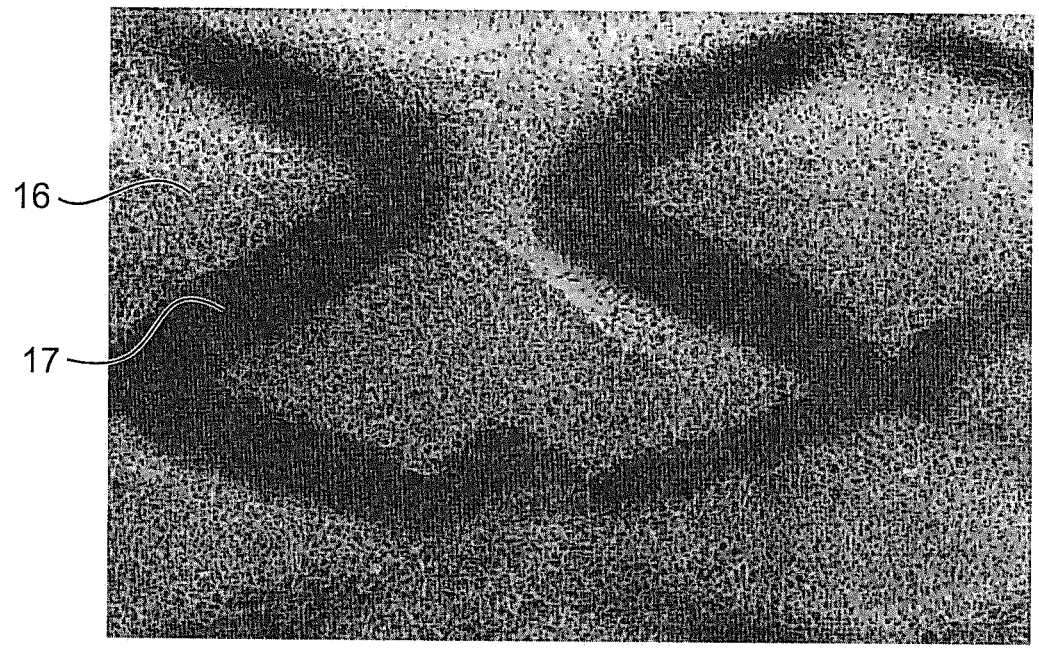
FIG. 11 shows a magnified view of the stent device of FIG. 10.

A magnified view of the optimal fiber alignment (FIG. 11) shows the strut adherence 16 and the center of the cell structure 17 and optimal orientation of circular and fibrous longitudinal fibers as well as angulations that form the optimal covering for the stent.

Figure 12:
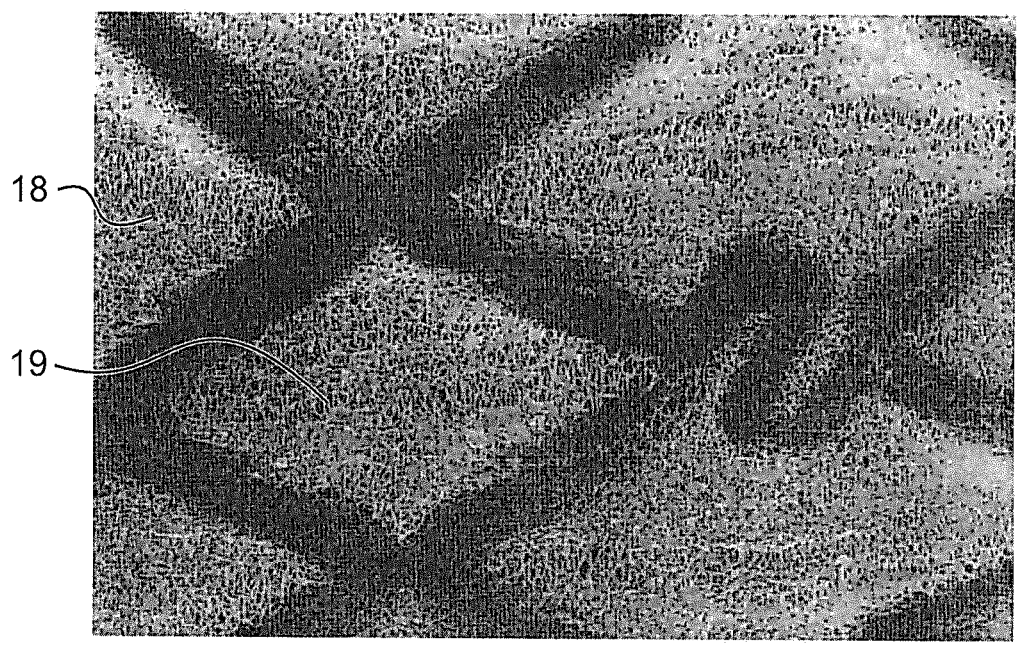
FIG. 12 shows the electrospun fibers on a stent device that has been expanded.
Figure 13A:
FIG. 13A-B shows a magnified view of the expanded stent device of FIG. 12.
Figure 13B:
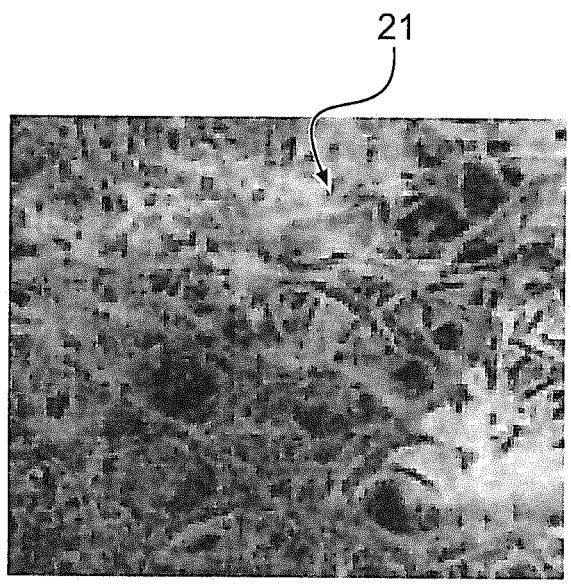

The configuration allows the fibers to maintain their integrity when the stent is expanded (FIG. 12), where the fibers maintain their optimal orientation in the expanded form, as seen in the center of the cells 18, 19. Further magnification of the expanded stent (FIG. 13) shows the optimal configuration of the fibers adhered to the strut of the stent 20. Yet further magnification shows that the structural fibers 21 are optimal for expansion and red blood cells or drug application.

Figure 14:
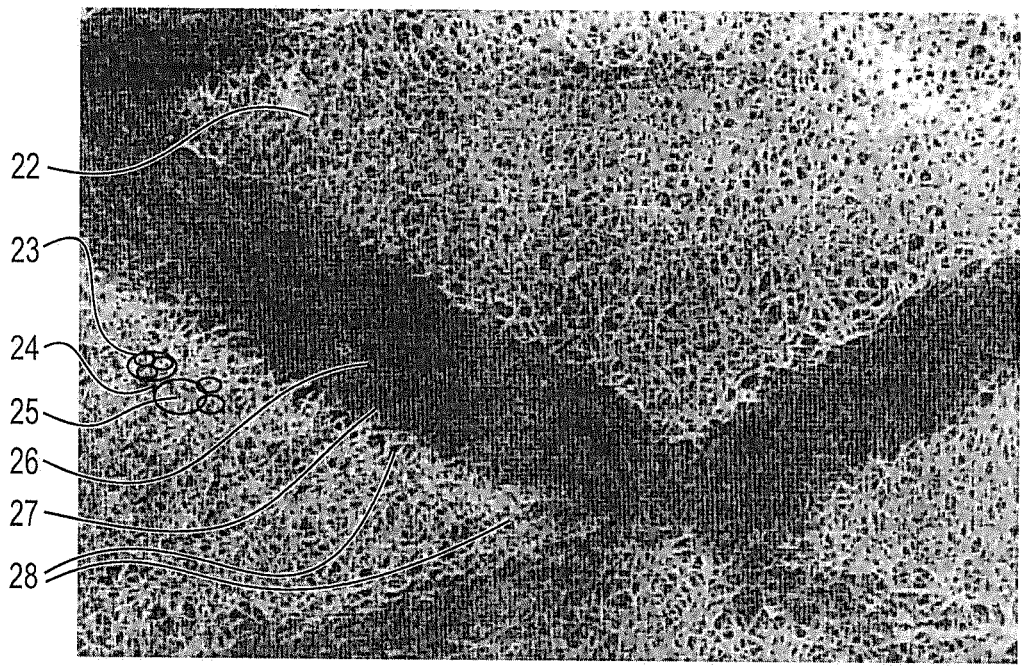
FIG. 14 shows the fibers on an electrospun stent device.
Figure 15:
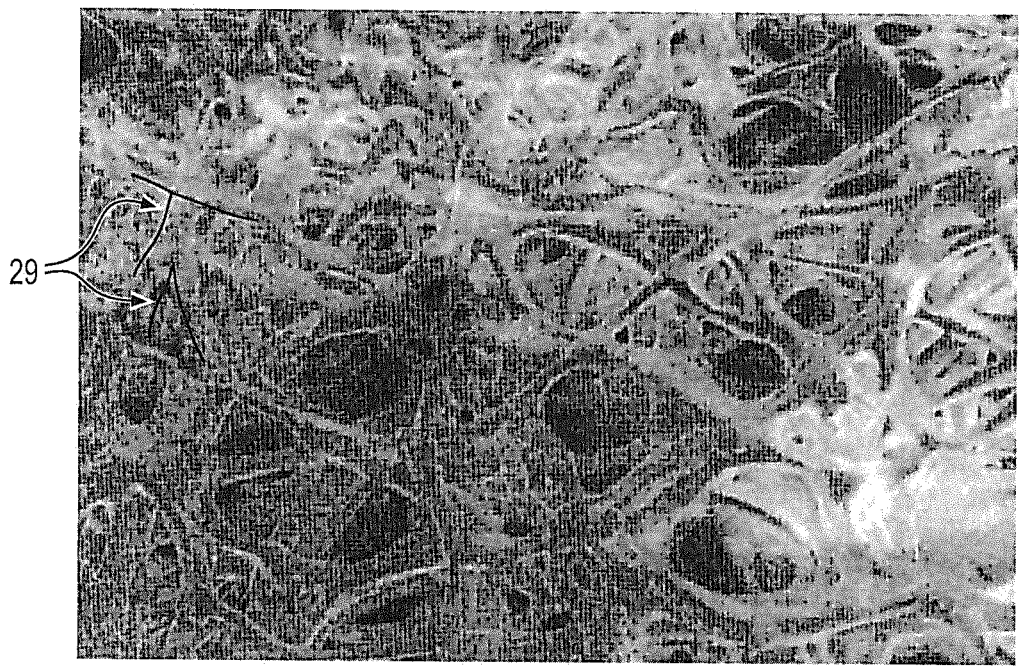
FIG. 15 shows a magnified view of the fibers of FIG. 14.

Magnification of fibers on an expanded stent (FIG. 14) show how the stretch coming off the struts and the various optimal shapes formed during the electrospinning process to allow for expansion. The shapes may include: a "Y" or "V" angulated connector 22 for optimal expansion, multiple circular connect rings of varying sizes 23, or a large base circle 24 that may be integrated with smaller base circles 25. The maximum density of the electrospun covering at center of the struts 26 tapers to a lower density away from the center of the struts 27 and to a lower density at the edges of the struts 28. A further magnified view of the stent covering (FIG. 15) shows the detailed view of the angulated mesh 29 allowing for optimal expansion.

Figure 16:
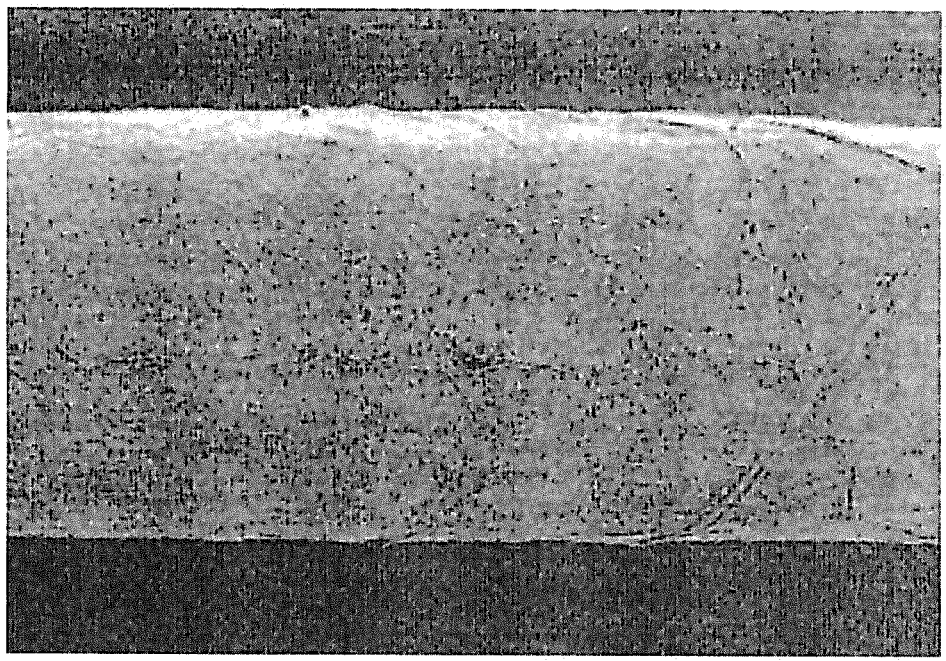
FIG. 16 shows a coated strut segment of a stent device.
Figure 17:
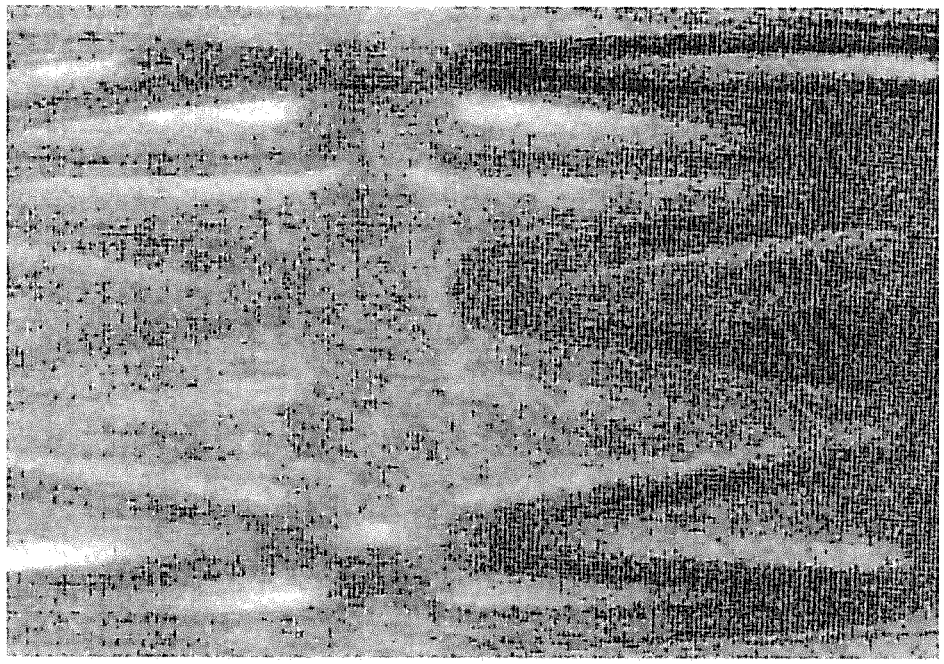
FIG. 17 shows an unexpanded stent device.
Figure 18:
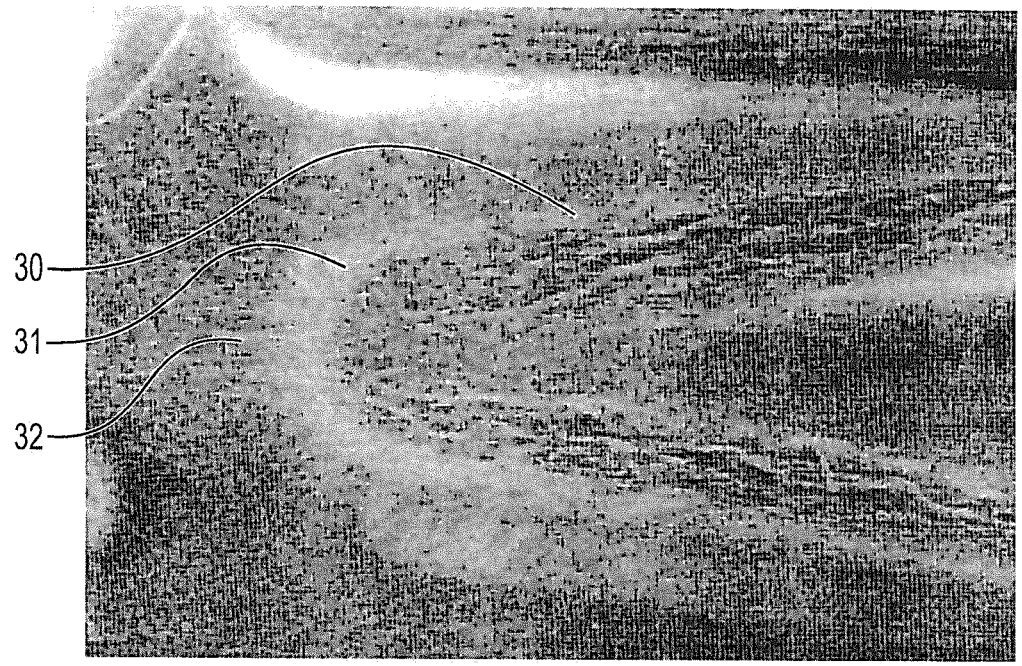
FIG. 18 shows an unexpanded stent device that has been coated.

FIG. 16 shows a magnified view of a coated strut segment, while FIG. 17 shows an unexpanded stent. Another view of a covered stent (FIG. 18) shows increased thickness close to stent strut 30, the elasticity of the polymer fibers connected to the strut segments 31 and the elongated connectivity 32.

Figure 19:
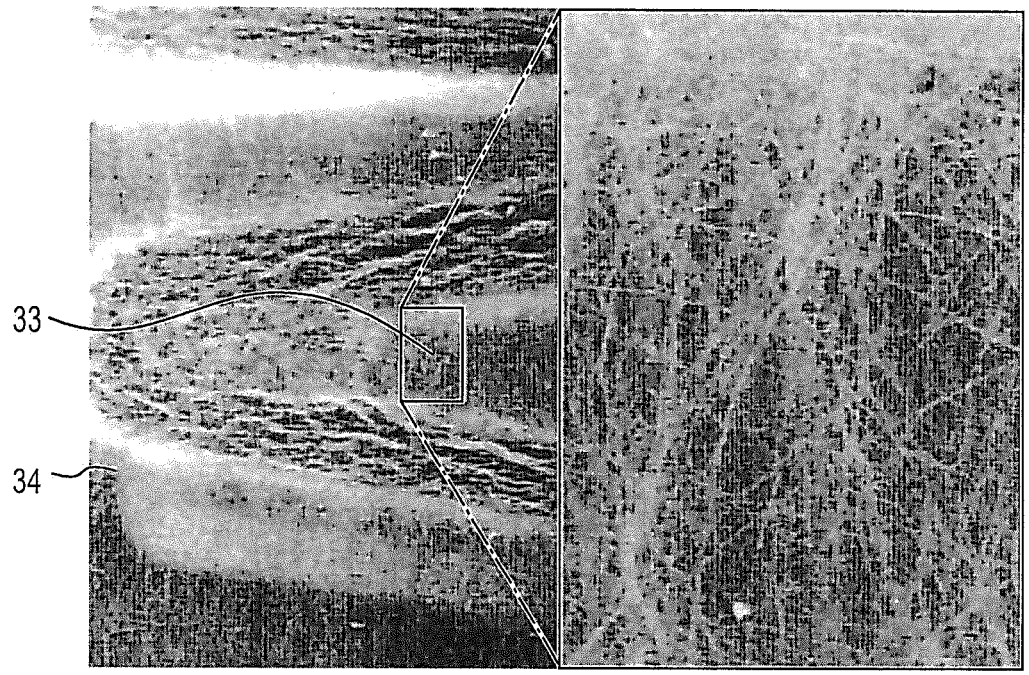
FIG. 19 shows an unexpanded stent device that has been coated.

Further magnification of an electrospun coated stent (FIG. 19) shows the thickness around strut segments 33, 34.

Figure 20:
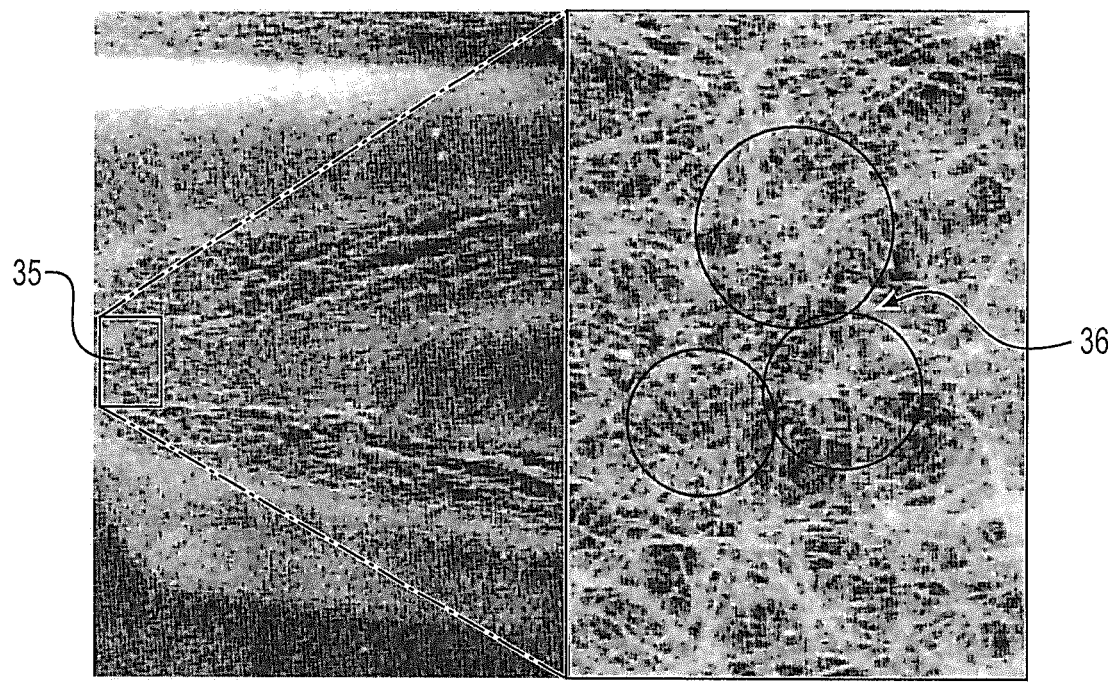
FIG. 20 shows a magnified view of the coated stent device of FIG. 19.

Close up of the stent with angles of 5% to 95% and circle combinations (FIG. 20) shows connectivity to covered stent fiber and directional covering 35 and the circle and fiber orientation and combination 36.

Figure 21:
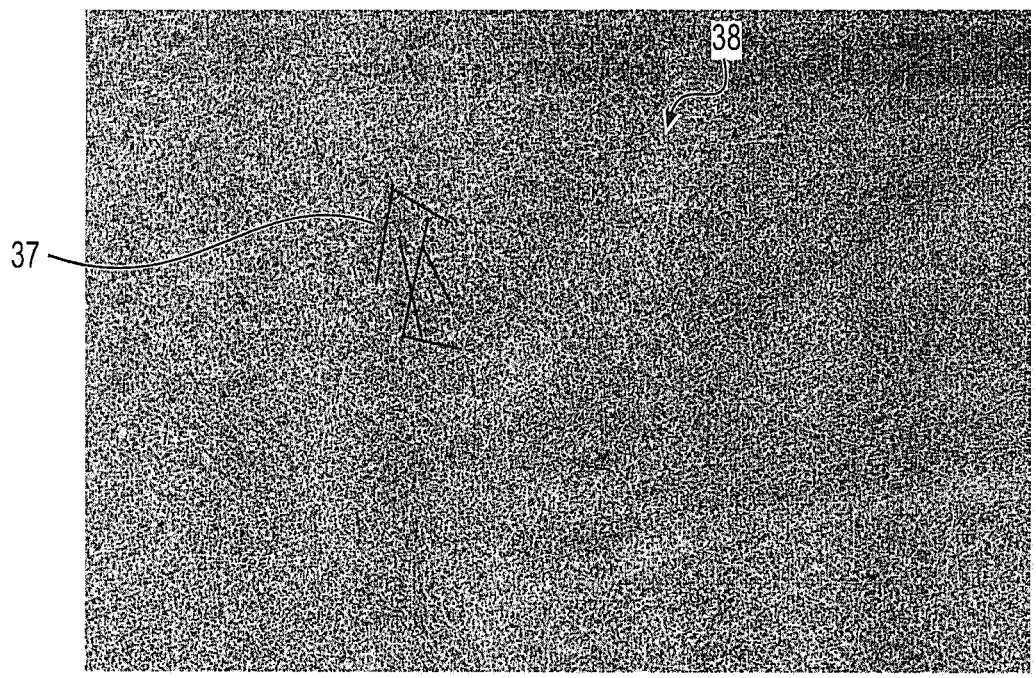
FIG. 21 shows an electrospun stent device.

A view of an electrospun stent (FIG. 21) shows angles in the covering at a macro level 37 and covered filaments 38.

Figure 22:
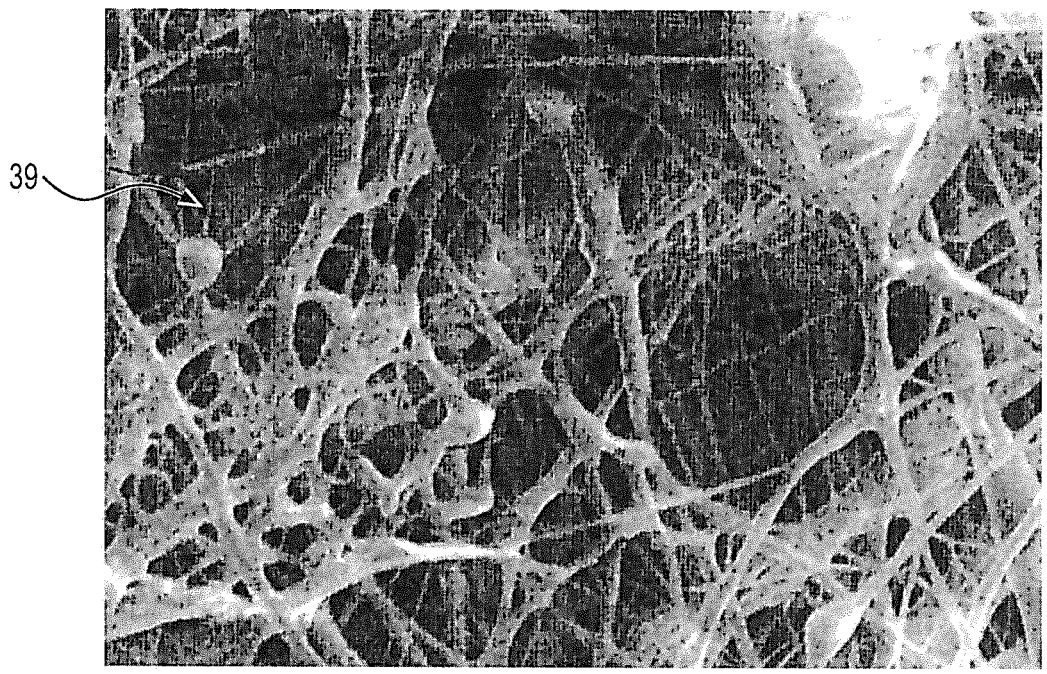
FIG. 22 shows a magnified view of the mesh structure on an electrospun stent device.
Figure 23:
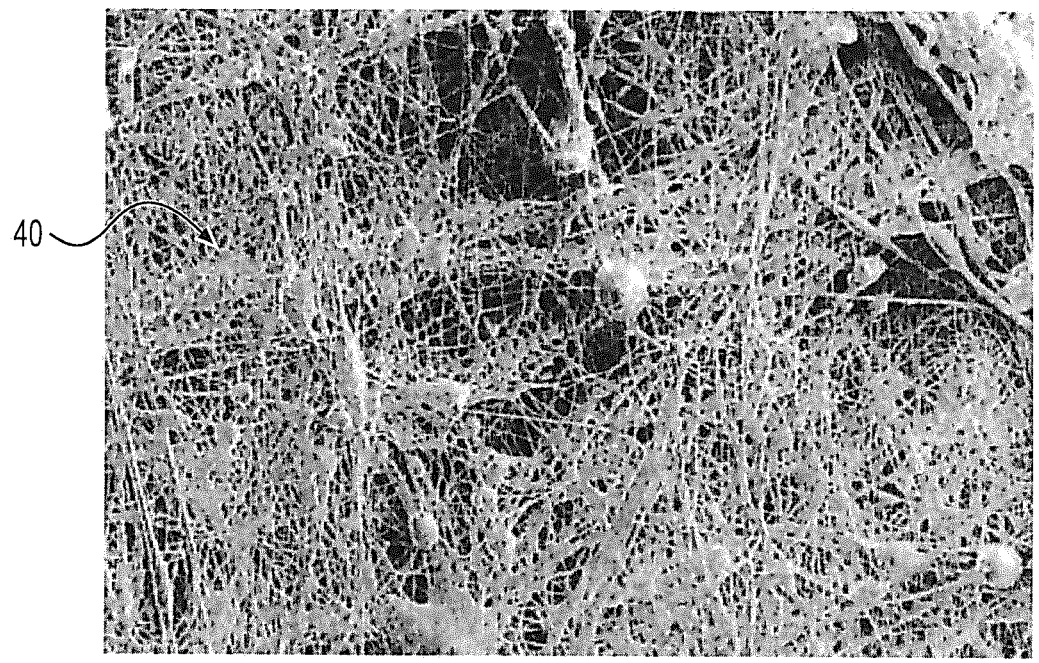
FIG. 23 shows a magnified view of the mesh structure on an electrospun stent device.
Figure 24:
FIG. 24 shows a magnified view of the mesh structure on an electrospun stent device.

A microscopic view of the mesh (FIG. 22) and the cross orientation that allows for expansion of the mesh shows a view of an expanded micro cell 39. A lower magnification (FIG. 23) of the same angle 40 is seen in an expanded view of the mesh. FIG. 24 shows an electrospun coating with a different orientation and filament thickness 41.

Figure 25:
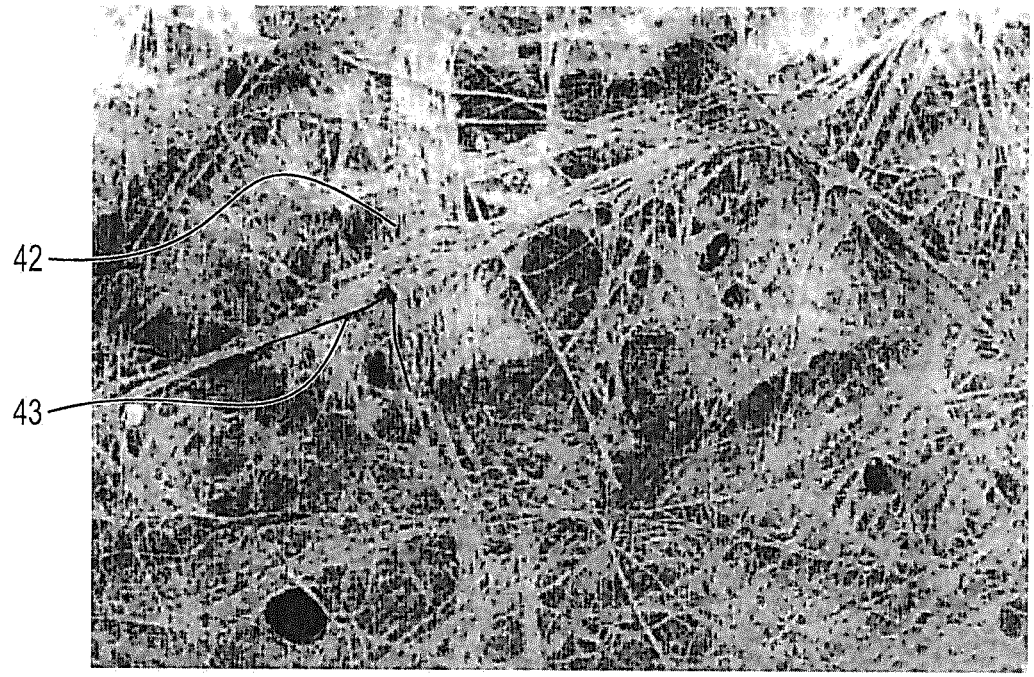
FIG. 25 shows a magnified view of the mesh structure on an electrospun stent device.

Electrospinning allows the formation of various fibers and angles with different filament thickness (FIG. 25). Additionally, variation of crystallinity by spinning the material on the device when the device is at a variant temperature of up to 38° C. above or below room temperature will have an impact on the formation of the patterns, adherence to the device, and filament roughness or smoothness. Based on a temperature change in the spinning process and a combination of a change in the device, the orientation patterns of the spun filaments as well as the elasticity of the filaments can be modified. For example, if the device is cold and the spun material is hot, this will substantially change the outcome versus if the device and the material are at the same temperature.

Variations in processing have an impact on changing the filament surface characteristics 42. Changing the surface quality of the filaments affects their ability to expand or to have more friction, depending on the actual surface quality of the filaments, which has a direct impact on the opening behavior of the device; smoother surface, easier opening, and less tearing of the filaments. Greater roughness of the fibers translates to a greater surface area coefficient of friction and the potential to increase risk of tearing or when there is a filament disruption for the others to maintain their integrity 43.

Figure 26:
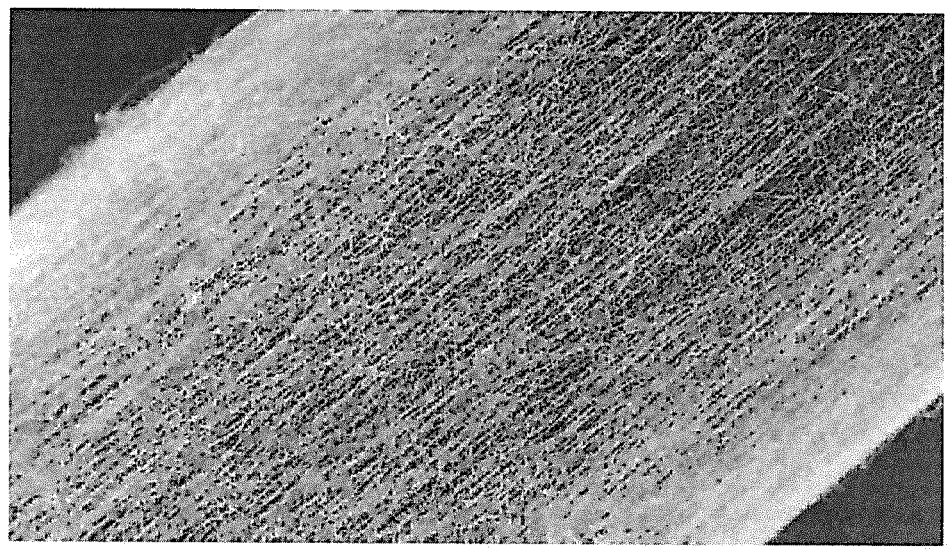
FIG. 26 shows a linear coating in a unidirectional form on a crimped stent device.
Figure 27:
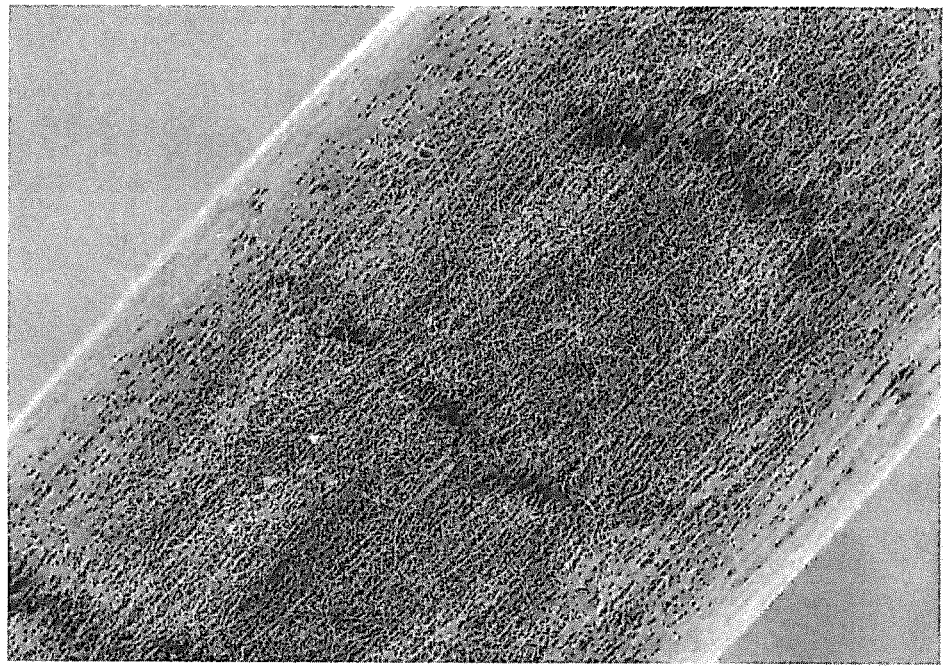
FIG. 27 shows partial expansion of a stent device having a linear coating in a unidirectional form.
Figure 28:
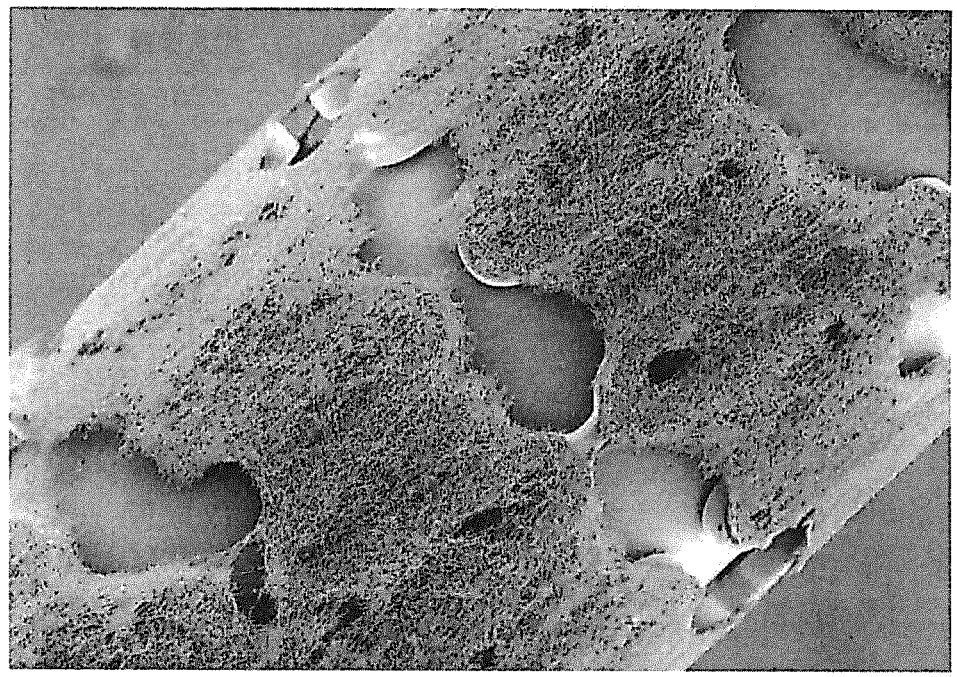
FIG. 28 shows further expansion of a stent device having a linear coating in a unidirectional form.

Electrospinning provides an advantage over linear coating of a stent in a unidirectional form (FIG. 26), because the linear coating does not provide a mesh which allows elasticity of the coating as the device is expanded. Accordingly, as a linear coated device is expanded, this lack of elasticity results in the destruction of the fibers (FIG. 27) and failure in the expanded stent (FIG. 28) to provide a surface capable of occluding an opening in a luminal vessel.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A method for occluding an opening in a luminal vessel, comprising:
    placing at said opening a device comprising:
        an expandable stent body comprising a plurality of cells formed by a set of struts, wherein each cell has a center and wherein the stent body is coated with a layer of biodegradable material comprising a biodegradable polymer, wherein at an area close to said stent body's struts the layer of biodegradable material is coated thicker relative to coating moving away from the stent body's struts towards the centers of each cell; and
        an electrospun fibrous covering comprising a biodegradable material, wherein the electrospun fibrous covering covers said layer of biodegradable material and said stent body for increased stability during placement, wherein said layer of biodegradable material promotes adherence of the electrospun fibrous covering, wherein fibers within said electrospun fibrous covering interlock and overlap forming shapes comprising angles and rings of varying sizes, wherein the layer of biodegradable material contains the same material as the biodegradable material of the electrospun fibrous covering, and
    wherein the electrospun fibrous covering covers at least a portion of the stent body; and
    expanding said stent body to immobilize said device at said opening.

2. The method of claim 1, wherein said luminal vessel is an artery or a vein.

3. The method of claim 1, wherein said opening is an aneurysm, perforation, rupture or fistula.

4. The method of claim 3, wherein the aneurysm is a berry aneurysm or a fusiform aneurysm.

5. The method of claim 3, wherein the aneurysm is a cerebral, cardiac, pulmonary or aortic aneurysm.

6. The method of claim 1, wherein said stent body comprises a biodegradable or bioabsorbable material.

7. The method of claim 6, wherein said biodegradable or bioabsorbable material comprises magnesium, iron or a polymer or co-polymer material.

8. The method of claim 1, wherein said stent body comprises a non-biodegradable or non-bioabsorbable material.

9. The method of claim 8, wherein the non-biodegradable or non-bioabsorbable material comprises stainless steel, cobalt chromium, or a non-degradable polymer.

10. The method of claim 1, wherein the electrospun fibrous covering comprises a poly-($\alpha$-hydroxy acid) or poly-(L-lactic acid).

11. A method for treating a condition in a luminal vessel in a subject, comprising:
    introducing into said subject a device comprising:
        an expandable stent body comprising a plurality of cells formed by a set of struts, wherein each cell has a center and wherein the stent body is coated with a layer of biodegradable material comprising a biodegradable polymer, wherein at an area close to said stent body's struts the layer of biodegradable material is coated thicker relative to coating moving away from the stent body's struts towards the centers of each cell; and
        an electrospun fibrous covering comprising a biodegradable material, wherein the electrospun fibrous covering covers said layer of biodegradable material and said stent body for increased stability during placement, wherein said layer of biodegradable material promotes adherence of the electrospun fibrous covering, wherein fibers within said electrospun fibrous covering interlock and overlap forming shapes comprising angles and rings of varying sizes, wherein the layer of biodegradable material contains the same material as the biodegradable material of the electrospun fibrous covering, and wherein the electrospun fibrous covering covers at least a portion of the stent body;
    positioning said device at a treatment site; and
    expanding said stent body to immobilize said device at the treatment site.

12. The method of claim 11, wherein said stent body comprises magnesium, iron or a polymer material.

13. The method of claim 11, wherein said condition is a plaque in a blood vessel.

14. The method of claim 11, wherein said condition is an acute myocardial infarction.

15. The method of claim 11, wherein said condition is a hole or an opening in said luminal vessel.

16. The method of claim 11, wherein said condition is a grafted vessel and wherein said device is emplaced under said grafted vessel to support the grafted vessel during a healing process and prevent leakage at sutures.

17. The method of claim 11, wherein said stent body comprises a biodegradable or bioabsorbable material.

18. The method of claim 17, wherein said biodegradable or bioabsorbable material comprises magnesium, iron or a polymer or co-polymer material.

19. The method of claim 11, wherein said stent body comprises a non-biodegradable or non-bioabsorbable material.

20. The method of claim 19, wherein the non-biodegradable or non-bioabsorbable material comprises stainless steel, cobalt chromium, or a non-degradable polymer.

21. The method of claim 11, wherein the electrospun fibrous covering comprises a poly-($\alpha$-hydroxy acid) or poly-(L-lactic acid).

* * * * *